US012802795B2

(12) United States Patent
Kido

(10) Patent No.: US 12,802,795 B2
(45) Date of Patent: Nov. 17, 2026

(54) INFORMATION PROCESSING APPARATUS

(71) Applicant: Hitachi, Ltd., Tokyo (JP)

(72) Inventor: Kunihiko Kido, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 87 days.

(21) Appl. No.: 18/868,086

(22) PCT Filed: Apr. 28, 2023

(86) PCT No.: PCT/JP2023/016810
§ 371 (c)(1),
(2) Date: Nov. 21, 2024

(87) PCT Pub. No.: WO2024/024200
PCT Pub. Date: Feb. 1, 2024

(65) Prior Publication Data
US 2026/0196319 A1 Jul. 9, 2026

(30) Foreign Application Priority Data
Jul. 28, 2022 (JP) ................................ 2022-120523

(51) Int. Cl.
*G16H 20/30* (2018.01)
*G16H 10/60* (2018.01)
*G16H 20/00* (2018.01)

(52) U.S. Cl.
CPC ............. *G16H 20/00* (2018.01); *G16H 10/60* (2018.01)

(58) Field of Classification Search
CPC .............................. G16H 20/00; G16H 10/60
See application file for complete search history.

(56) References Cited

U.S. PATENT DOCUMENTS

2006/0173663 A1 8/2006 Langheier et al.
2014/0279754 A1 9/2014 Barsoum et al.
(Continued)

FOREIGN PATENT DOCUMENTS

EP 3531425 A1 8/2019
JP 2008-532104 A 8/2008
(Continued)

OTHER PUBLICATIONS

Chesnaye NC et al. "An introduction to inverse probability of treatment weighting in observational research", published on PubMed Central. https://pmcncbi.nlm.nih.gov/articles/PMC8757413/ (Year: 2021).*
(Continued)

*Primary Examiner* — Maroun P Kanaan
(74) *Attorney, Agent, or Firm* — PROCOPIO, CORY, HARGREAVES & SAVITCH LLP

(57) ABSTRACT

Provided is an information processing apparatus capable of improving reliability of a treatment effect by an output treatment method. An information processing apparatus using a treatment method output model that outputs a treatment method according to a state of a patient includes a treatment effect prediction model construction unit that constructs a treatment effect prediction model that includes the treatment method output model as a component, and compares a treatment effect when the treatment method is used with a treatment effect when the treatment method is not used, and a model adjustment unit that generates a prediction model group by inactivating a weighting factor of the treatment effect prediction model based on a tendency score when the treatment method is used and when the treatment method is not used, and adjusts the treatment method output model that is the component of the treatment effect prediction model such that a variance of a treatment
(Continued)

effect output from the prediction model group falls within a predetermined range.

20 Claims, 8 Drawing Sheets

(56) References Cited

U.S. PATENT DOCUMENTS

| | | | | |
|---|---|---|---|---|
| 2021/0241909 | A1 | 8/2021 | Bulut et al. | |
| 2022/0222554 | A1 | 7/2022 | Liu et al. | |
| 2023/0197240 | A1* | 6/2023 | Rosenberg | A61H 1/0214 705/2 |
| 2023/0352138 | A1* | 11/2023 | Fisher | G16H 50/20 |

FOREIGN PATENT DOCUMENTS

| | | | |
|---|---|---|---|
| JP | 2016-519807 | A | 7/2016 |
| WO | 2017/210502 | A1 | 12/2017 |
| WO | 2021/067733 | A1 | 4/2021 |

OTHER PUBLICATIONS

Patent Cooperation Treaty, International Search Report, Application No. PCT/JP2023/016810, dated Jul. 18, 2023, in 2 pages.

Extended European Search Report issued in European Application No. 23845939.0 dated Jun. 19, 2026, in 10 pages.

* cited by examiner

INFORMATION PROCESSING APPARATUS

TECHNICAL FIELD

The present invention relates to an information processing apparatus using a model that outputs a treatment method according to a state of a patient, and particularly relates to a technique for updating the model.

BACKGROUND ART

Digital therapy (hereinafter, DTx), which is an information processing apparatus using a model that is constructed by machine learning of known data and outputs a treatment method according to the state of a patient, has been developed. Since DTx can collect data in real time after launch, it is possible to update the model based on the collected data.

PTL 1 discloses obtaining a predicted value of a clinical parameter from a set of a model with the highest accuracy, which is selected according to a predictor from among a plurality of models, and the predictor, and updating the model according to the obtained predicted value and the measured value of the clinical parameter to improve the accuracy.

CITATION LIST

Patent Literature

PTL 1: JP 2016-519807 A

SUMMARY OF INVENTION

Technical Problem

However, in PTL 1, consideration is not given to improvement of the reliability of the model. That is, even if a treatment method having a high treatment effect is output by the updated model, the treatment effect may vary due to a slight change in the predictor.

Therefore, an object of the present invention is to provide an information processing apparatus capable of improving reliability of a treatment effect by an output treatment method.

Solution to Problem

In order to achieve the above object, the present invention is an information processing apparatus using a treatment method output model that outputs a treatment method according to a state of a patient, the information processing apparatus including a treatment effect prediction model construction unit that constructs a treatment effect prediction model that includes the treatment method output model as a component, and compares a treatment effect when the treatment method is used with a treatment effect when the treatment method is not used, and a model adjustment unit that generates a prediction model group by inactivating a weighting factor of the treatment effect prediction model based on a tendency score when the treatment method is used and when the treatment method is not used, and adjusts the treatment method output model that is the component of the treatment effect prediction model such that a variance of a treatment effect output from the prediction model group falls within a predetermined range.

Advantageous Effects of Invention

According to the present invention, it is possible to provide an information processing apparatus capable of improving reliability of a treatment effect by an output treatment method.

DESCRIPTION OF EMBODIMENTS

Hereinafter, embodiments of an information processing apparatus according to the present invention will be described with reference to the accompanying drawings. Note that, in the following description and the accompanying drawings, components having the same functional configuration are denoted by the same reference signs, and repetitive description will be omitted.

Example 1

Figure 1:
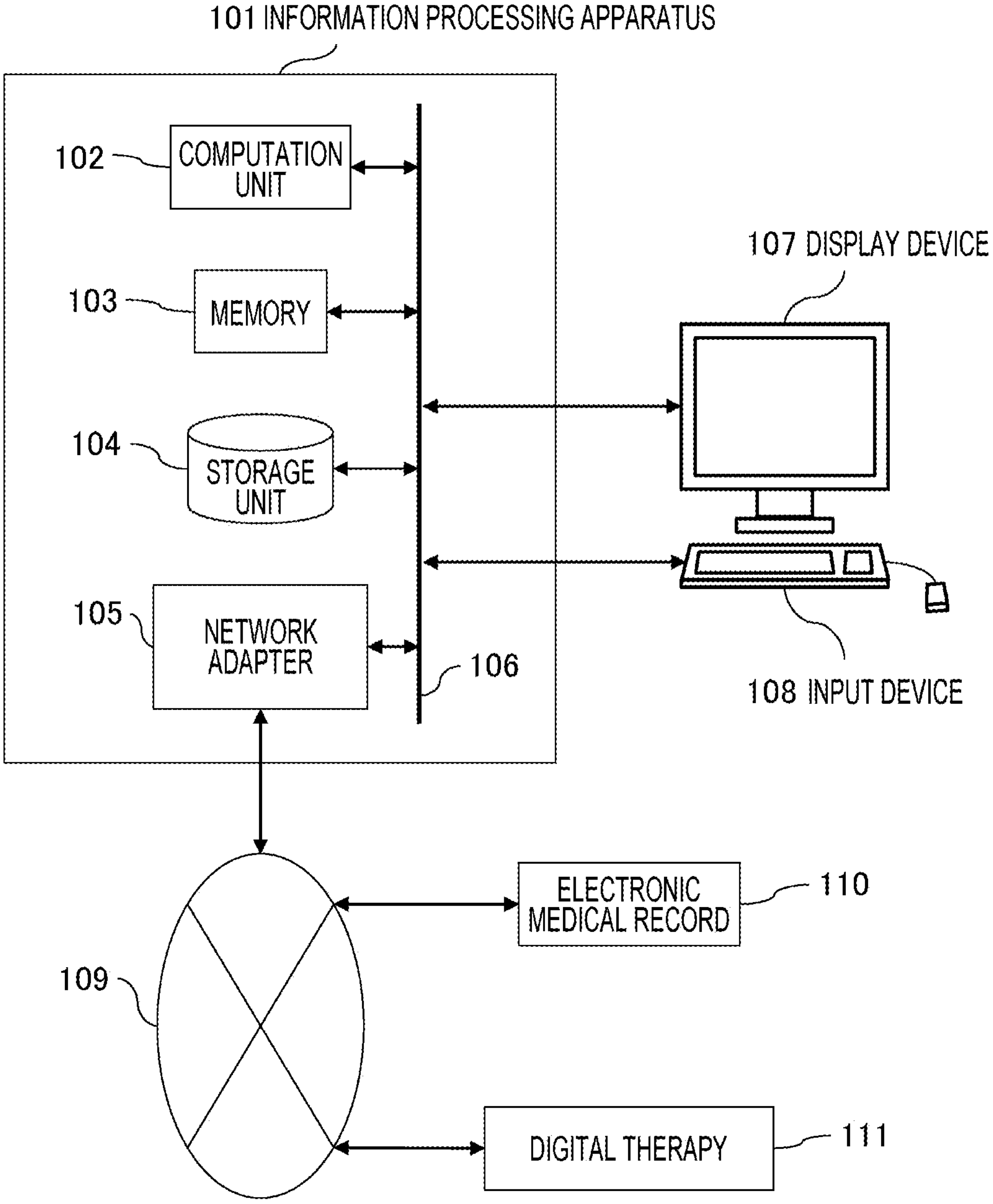
FIG. 1 is an overall configuration diagram of an information processing apparatus.

FIG. 1 is a diagram illustrating a hardware configuration of an information processing apparatus 101. The information processing apparatus 101 is configured such that a computation unit 102, a memory 103, a storage unit 104, and a network adapter 105 are connected by a system bus 106 to be able to transmit and receive signals. In addition, the information processing apparatus 101 is connected to an electronic medical record 110 and a digital therapy 111 via a network 109 to be able to transmit and receive signals. Further, a display device 107 and an input device 108 are connected to the information processing apparatus 101. Here, "being able to transmit and receive signals" indicates a state in which signals can be transmitted and received to and from each other or from one to the other electrically and optically regardless of a wired manner or a wireless manner.

The computation unit 102 is a device that controls the operation of each component, and is specifically a central processing unit (CPU), a micro processor unit (MPU), or the like. The computation unit 102 loads a program stored in the storage unit 104 and data necessary for executing the program into the memory 103, executes the program, and performs various types of processing on the program. The memory 103 stores programs to be executed by the computation unit 102 and the progress of computation processing. The storage unit 104 is a device that stores a program executed by the computation unit 102 and data necessary for executing the program, and is specifically a hard disk drive (HDD), a solid state drive (SSD), or the like. The network adapter 105 is provided for connecting the information processing apparatus 101 to the network 109 such as a LAN, a telephone line, or the Internet. Various types of data handled by the computation unit 102 may be transmitted and received to and from the outside of the information processing apparatus 101 via the network 109 such as a local area network (LAN).

The display device 107 is a device that displays a processing result or the like of the information processing apparatus 101, and is specifically a liquid crystal display or the like. The input device 108 is an operation device with which an operator gives an operation instruction to the information processing apparatus 101, and is specifically a keyboard, a mouse, a touch panel, or the like. The mouse may be another pointing device such as a track pad or a track ball.

The electronic medical record 110 stores medical data related to a patient, for example, data related to a state of the patient and a treatment effect for a certain treatment method. The digital therapy 111 has a treatment method output model that is a model for outputting a treatment method according to the state and profile of a patient.

Figure 2:
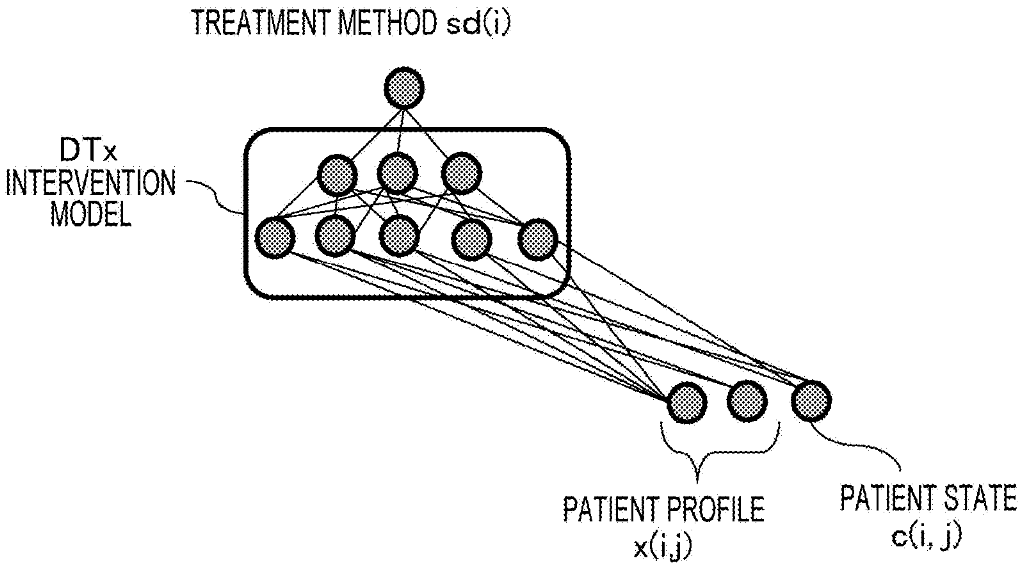
FIG. 2 is a diagram illustrating an example of a DTx intervention model that is a model for outputting a treatment method according to a state of a patient.

An example of a DTx intervention model that is the treatment method output model will be described with reference to FIG. 2. The DTx intervention model is a model that outputs a treatment method sd(i) according to a patient profile x(i, j) and a patient state c(i, j), and is a neural network constructed by machine learning of known data. Note that i is an index for specifying a patient, j is an index representing a patient state or a type of patient profile. The patient state is calorie intake or exercise amount, and the patient profile is gender, age, or the like. In addition, the treatment method output from the DTx intervention model is, for example, a type of medicine.

Figure 3:
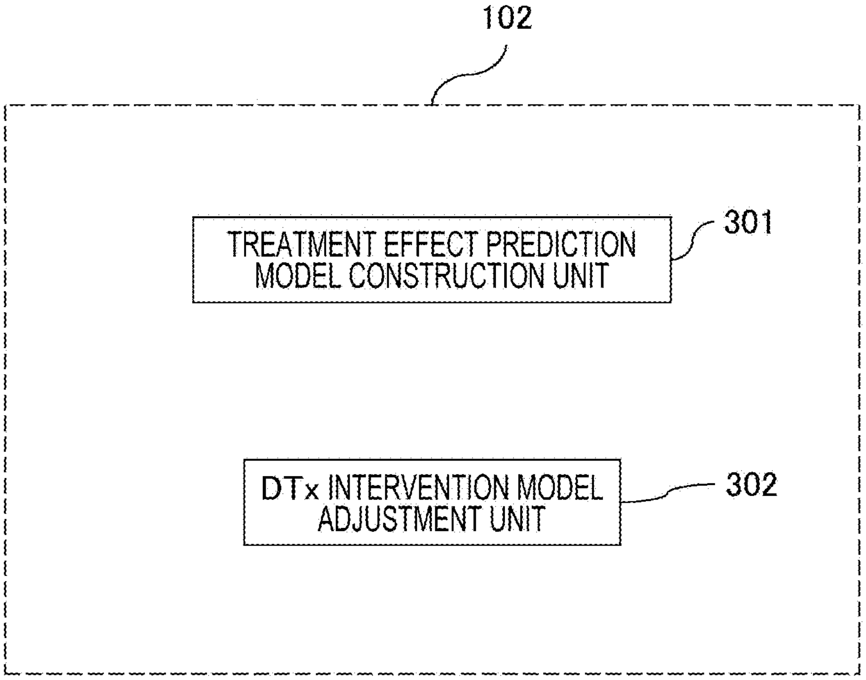
FIG. 3 is a diagram illustrating an example of functional blocks of Example 1.

Functional blocks of Example 1 will be described with reference to FIG. 3. Note that the functional blocks may be configured by dedicated hardware or may be configured by software that operates on the computation unit 102. In the following description, a case where the functional blocks of Example 1 are configured by software will be described. In Example 1, a treatment effect prediction model construction unit 301 and a DTx intervention model adjustment unit 302 are provided. Each unit will be described below.

The treatment effect prediction model construction unit 301 constructs a treatment effect prediction model that compares a treatment effect when the treatment method output from the DTx intervention model is used with a treatment effect when the treatment method is not used.

The DTx intervention model adjustment unit 302 adjusts the DTx intervention model to reduce the variance of the treatment effect when the treatment method output from the DTx intervention model is used.

Figure 4:
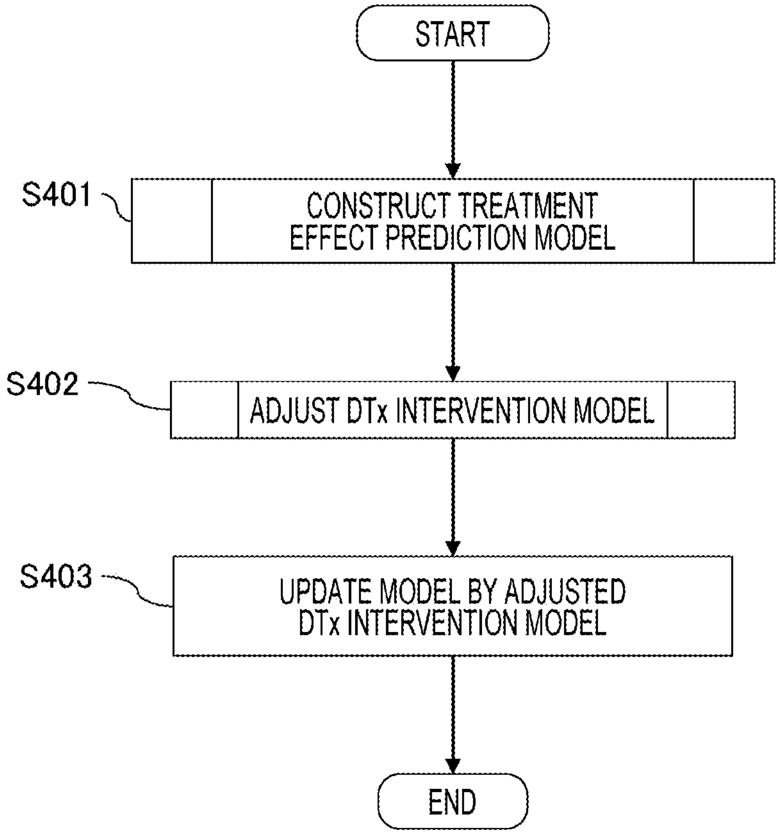
FIG. 4 is a diagram illustrating an example of a flow of processing of Example 1.

An example of a flow of processing performed in Example 1 will be described for each step with reference to FIG. 4.

(S401)

The treatment effect prediction model construction unit 301 constructs a treatment effect prediction model.

An example of a flow of processing performed in S401 will be described for each step with reference to FIG. 5.

(S501)

The treatment effect prediction model construction unit 301 acquires a DTx intervention model. For example, the DTx intervention model is transmitted from the digital therapy 111.

(S502)

Figure 6:
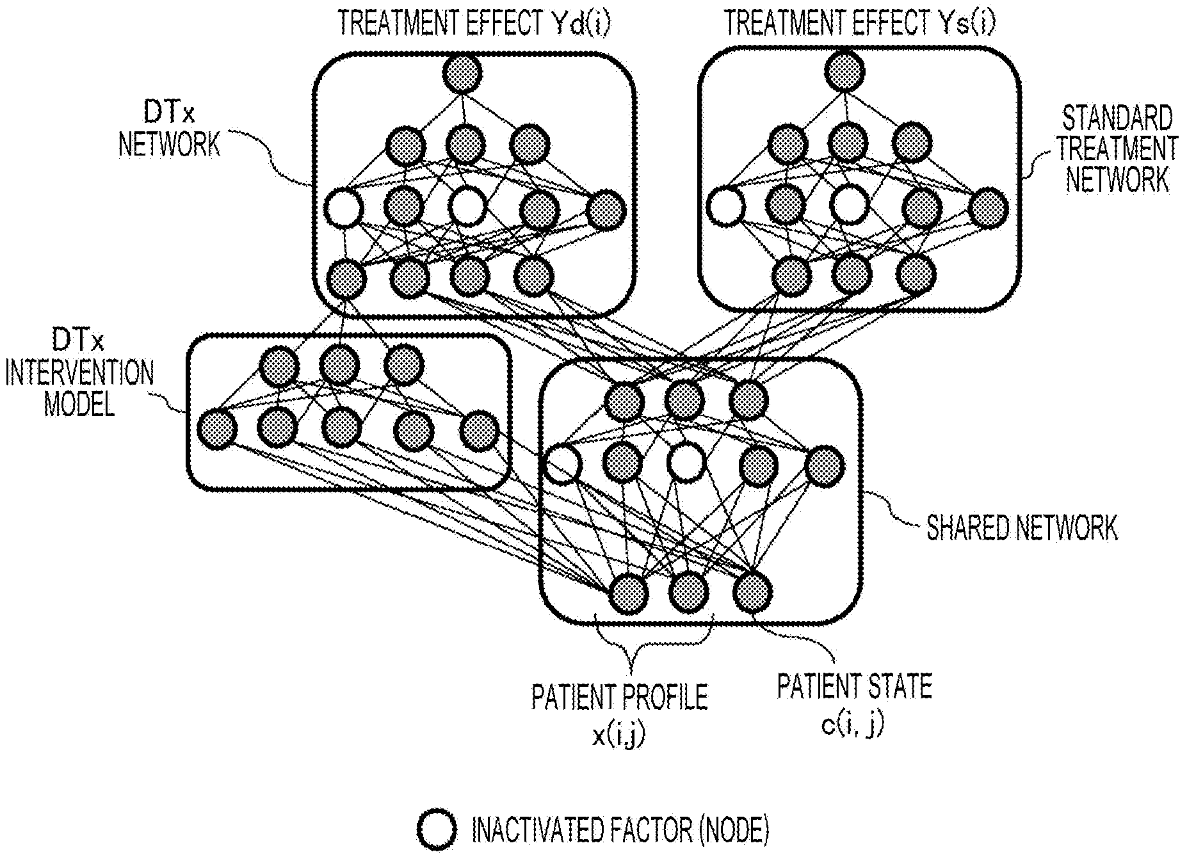
FIG. 6 is a diagram illustrating an example of the treatment effect prediction model.

The treatment effect prediction model construction unit 301 constructs a treatment effect prediction model illustrated in FIG. 6 by connecting the DTx intervention model acquired in S501 to three networks of a DTx network, a standard treatment network, and a shared network. The DTx network outputs the predicted value of the treatment effect when the treatment method output from the DTx intervention model is used. The standard treatment network outputs the predicted value of the treatment effect when the treatment method output from the DTx intervention model is not used. The shared network outputs parameters shared between the DTx network and the standard treatment network, depending on the patient profile x(i, j) and the patient state c(i, j).

(S503)

The treatment effect prediction model construction unit 301 inputs the patient profile x(i, j) and the patient state c(i, j) of the collected data to the treatment effect prediction model and outputs the predicted value of the treatment effect. The predicted value of the treatment effect is output for each of a case where the treatment method output from the DTx intervention model is used and a case where the treatment method is not used. Here, regarding the unevenness of the patient background when the treatment method output from the DTx intervention model is used and when the treatment method is not used, such as a case where the age of a patient group using the treatment method output from the DTx intervention model is young, a weighting factor of the treatment effect prediction model is inactivated based on the tendency score for both a case where the treatment method output from the DTx intervention model is used and when the treatment method is not used, and the treatment effect prediction model is constructed while the unevenness of the patient background is corrected. The tendency score p(i) is calculated using, for example, the following expression.

$$p(i) \sim 1/(1 + \exp(-(a_1 \times (i,1) + a_2 \times (i,2) + \ldots + b_1 c(i,1) + b_2 c(i,2) + \ldots + e))) \quad \text{[Math. 1]}$$

Here, $a_1, a_2, \ldots, b_1, b_2, \ldots$ are coefficients calculated from the collected data.

In addition, the weighting factor to be inactivated based on the tendency score p(i) is represented by the following expression.

$$r(l)_{ss}, r(l)_{i,d}, r(l)_{i,s} \sim Bernoulli(1 - \gamma/2 - H(p(i))/2) \quad \text{[Math. 2]}$$

$$\text{Where, } H(p(i)) = -p(i)\log(p(i)) - (1-p(i))\log(1-p(i))$$

Here, $r(l)_{ss}$ is a weighting factor of an l layer of the shared network, $r(l)_{i,d}$ is a weighting factor of the l layer of the DTx network, $r(l)_{i,s}$ is a weighting factor of the l layer of the standard treatment network, and y is an offset hyperparameter and is usually set to 1.

In addition, the treatment effect prediction model illustrated in FIG. 6 is represented by the following expression.

$$s^{\sim}(x) = f\left(\ldots\ f\left(r(l)_{ss} \odot (w(l)_{ss})^T (x, c)\right)\ \ldots\right)$$ [Math. 3]

$$r\,(l)_s \sim Bernoulli(q)$$

$$sd^{\sim}(x) = f\left(\ldots\ f\left(r(l)_s \odot (w(l)_{ssd})^T (x, c))\right)\ \ldots\right)$$

$$Yd^{\sim} = f\left(\ldots\ f\left(r(l)_{i,d} \odot \left(w(l)_{i,d}\right)^T (s^{\sim}((x, c)), sd^{\sim}((x, c)))\ \ldots\right)$$

$$Ys^{\sim} = f\left(\ldots\ f\left(r(l)_{i,s} \odot \left(w(l)_{i,s}\right)^T s^{\sim}((x, c))\right)\ \ldots\right)$$

Here, s~(x) is the shared network, sd~(x) is the DTx intervention model, Yd~ is the DTx network, Ys~ is the standard treatment network, and f(•) is an activation function.

(S504)

The treatment effect prediction model construction unit 301 adjusts the coefficient of the treatment effect prediction model based on a loss function regarding an error of the predicted value for the treatment effect included in the collected data. That is, the coefficient is adjusted so that the output of the loss function becomes smaller. For example, a square error function is used as the loss function, and for example, a stochastic gradient method or the like is used to adjust the coefficient.

(S505)

The treatment effect prediction model construction unit 301 determines whether or not an end condition is satisfied. When the end condition is satisfied, the processing flow ends, and when the end condition is not satisfied, the processing returns to S503. The end condition is, for example, a predetermined number of repetitions, a threshold value for the output of the loss function, or a threshold value for the amount of change in the output of the loss function.

Figure 5:
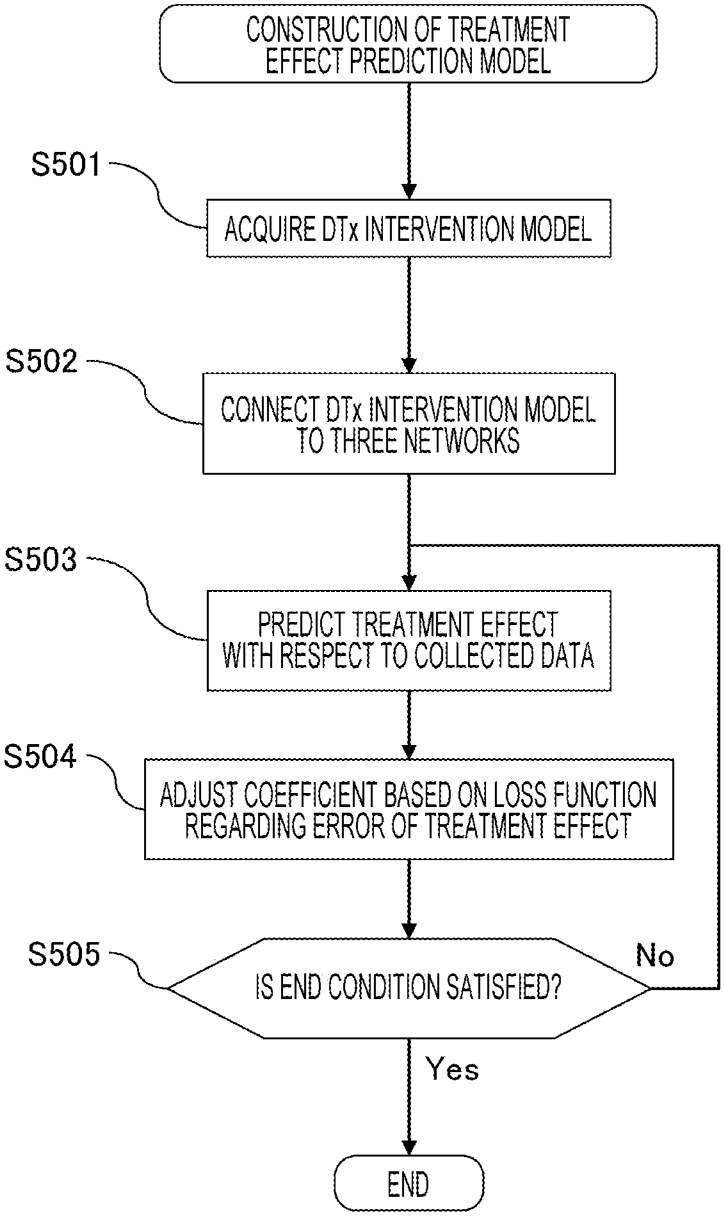
FIG. 5 is a diagram illustrating an example of a flow of processing of constructing a treatment effect prediction model.

With the flow of processing illustrated in FIG. 5, the treatment effect prediction model in which coefficients are adjusted according to newly collected data is constructed. The description returns to FIG. 4.

(S402)

The DTx intervention model adjustment unit 302 adjusts the DTx intervention model to reduce the variance of the treatment effect when the treatment method output from the DTx intervention model is used.

An example of a flow of processing performed in S402 will be described for each step with reference to FIG. 7.

(S701)

Figure 8:
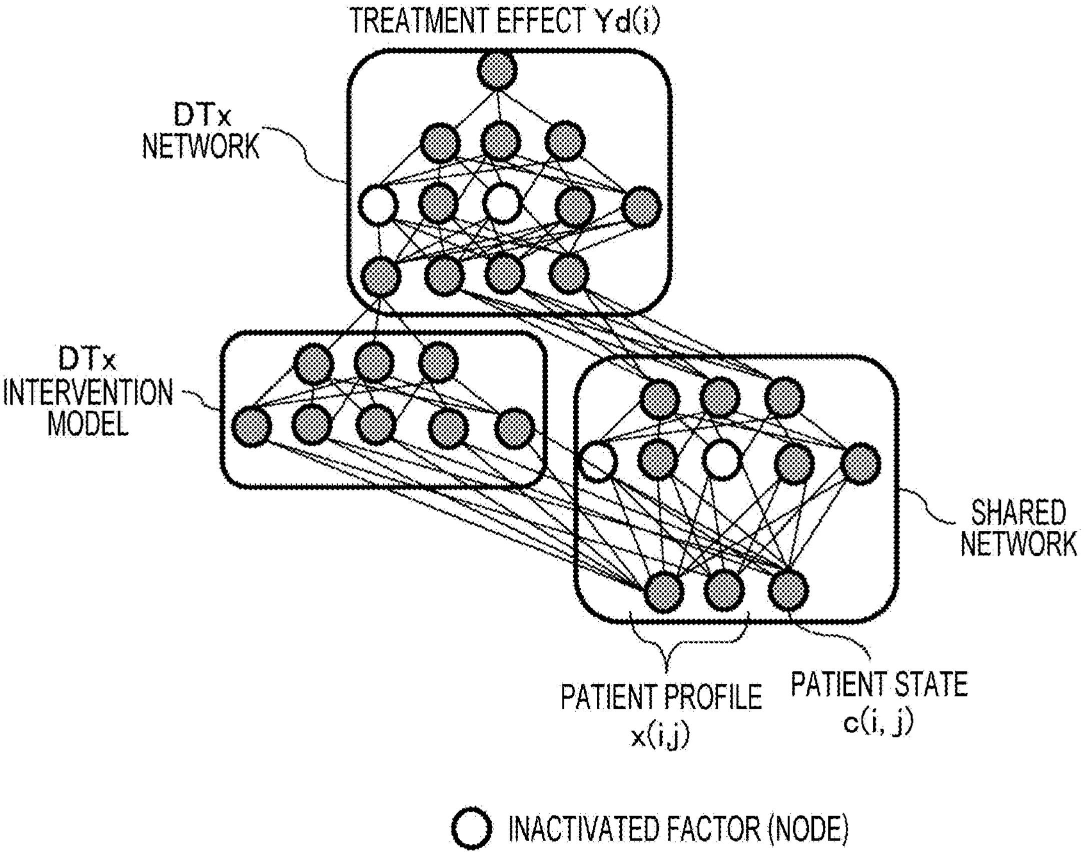
FIG. 8 is a diagram illustrating an example of the treatment effect prediction model used to adjust the DTx intervention model.

The DTx intervention model adjustment unit 302 deletes the standard treatment network from the treatment effect prediction model constructed in S401, and constructs a treatment effect prediction model used to adjust the DTx intervention model. FIG. 8 illustrates a treatment effect prediction model used to adjust the DTx intervention model.

(S702)

The DTx intervention model adjustment unit 302 inactivates the weighting factor of the treatment effect prediction model to be used to adjust the DTx intervention model based on the tendency score for when the treatment method output from the DTx intervention model is used and when the treatment method is not used, and generates a prediction model group. Such a tendency score is calculated by the treatment effect prediction model construction unit 301. Note that the tendency score is calculated using Math. 1, and the weighting factor to be inactivated is represented by Math. 2.

(S703)

The DTx intervention model adjustment unit 302 inputs the patient profile x(i, j) and the patient state c(i, j) of the newly collected data to each of the prediction model groups generated in S702, and outputs the predicted value of the treatment effect.

(S704)

The DTx intervention model adjustment unit 302 adjusts the coefficients of the DTx intervention model based on the loss function regarding the variance of the predicted value output in S703. That is, the coefficients of the DTx intervention model are adjusted so that the variance of the predicted value becomes smaller. For example, a square error function is used as the loss function, and for example, a stochastic gradient method or the like is used to adjust the coefficient.

(S705)

The DTx intervention model adjustment unit 302 determines whether or not the end condition is satisfied. When the end condition is satisfied, the processing flow ends, and when the end condition is not satisfied, the processing returns to S703. The end condition is, for example, a predetermined number of repetitions, a threshold value for the output of the loss function, or a threshold value for the amount of change in the output of the loss function.

Figure 7:
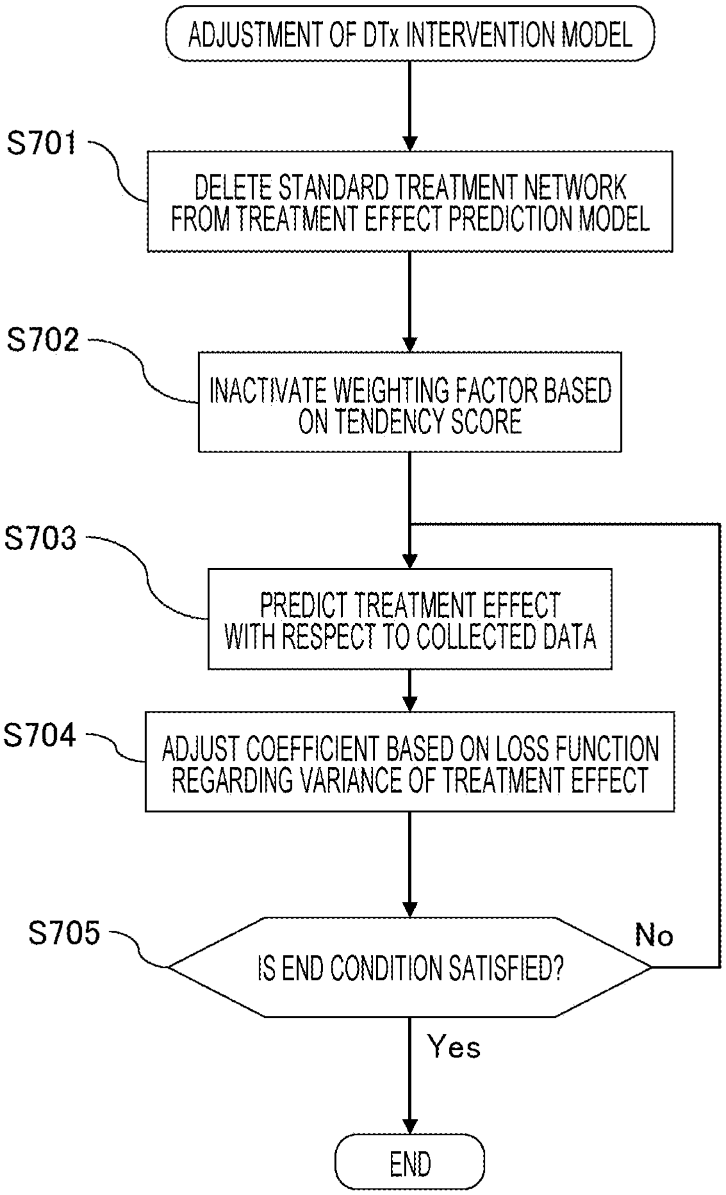
FIG. 7 is a diagram illustrating an example of a flow of processing of adjusting the DTx intervention model.

With the flow of processing illustrated in FIG. 7, the treatment effect prediction model in which coefficients are adjusted according to newly collected data is constructed. The description returns to FIG. 4.

(S403)

The model is updated by the DTx intervention model adjusted by the DTx intervention model adjustment unit 302.

With the flow of processing described above, it is possible to improve the reliability of the treatment effect by the treatment method output from the DTx intervention model. Note that the treatment effect obtained by the updated model may be displayed on the display device 107.

An example of a result display screen displayed on the display device 107 will be described with reference to FIG. 9. The result display screen illustrated in FIG. 9 includes a model update start button 901 and a result display portion 902.

The model update start button 901 is pressed when new data is collected and the DTx intervention model is updated.

The result display portion 902 displays the treatment effect obtained by the updated DTx intervention model. The treatment effect is displayed, for example, in a graph form in which the vertical axis indicates the frequency and the horizontal axis indicates the amount of effect. In addition, the treatment effect obtained by the DTx intervention model before update or the standard treatment may be displayed together. The effect of the model update becomes clear as the treatment effects obtained by the DTx intervention model before and after the update and the standard treatment are displayed together.

Figure 9:
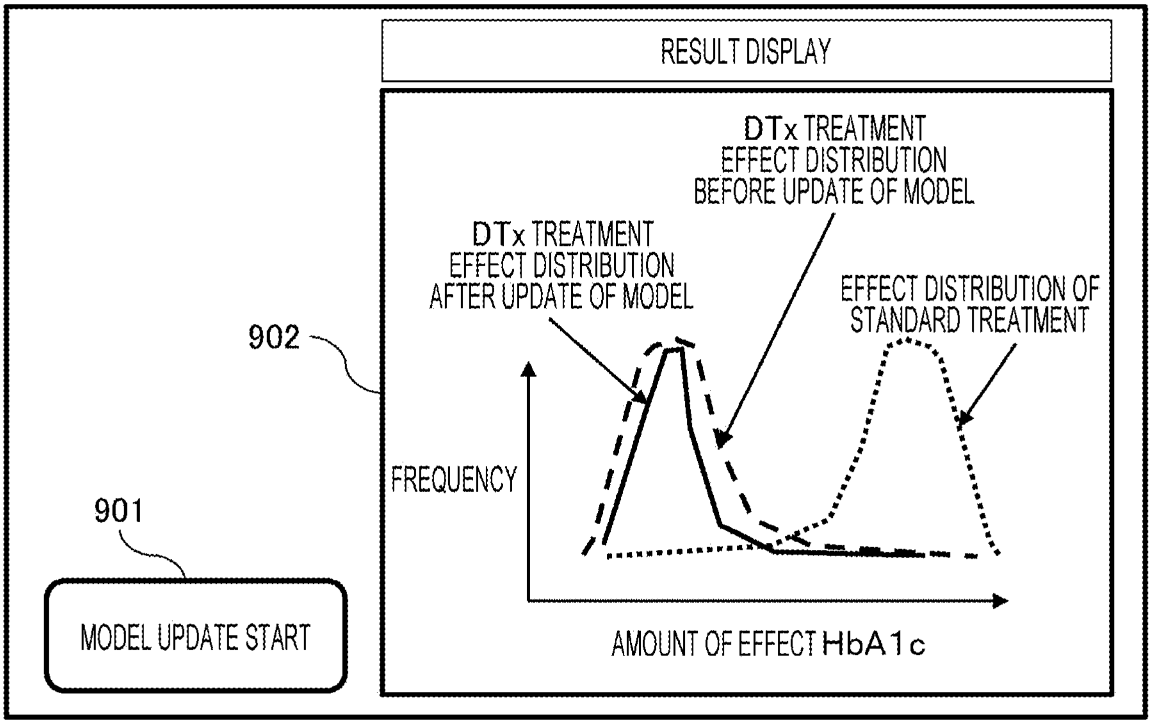
FIG. 9 is a diagram illustrating an example of a result display screen.

Note that the horizontal axis of the graph illustrated in FIG. 9 is HbAlc indicating the ratio of glycosylated hemoglobin, and it is indicated that the treatment method output from the DTx intervention model was able to reduce HbAlc as compared with the standard treatment. In addition, the distribution of the treatment effect obtained by the DTx intervention model after the update is narrower than that before the update, and it is indicated that it is possible to reduce the variation of the treatment effect and to improve the reliability.

Example of the present invention will be described above. The present invention is not limited to the above embodiment, and can be embodied by modifying the components without departing from the gist of the invention. In addition, a plurality of components disclosed in the above example may be appropriately combined. Further, some components may be deleted from all the components described in the above example.

REFERENCE SIGNS LIST

101 information processing apparatus
102 computation unit
103 memory
104 storage unit
105 network adapter
106 system bus
107 display device
108 input device
109 network
110 electronic medical record
111 digital therapy
301 treatment effect prediction model construction unit
302 DTx intervention model adjustment unit
901 model update start button
902 result display portion

The invention claimed is:

1. An information processing apparatus using a treatment method output model that outputs a treatment method according to a state of a patient, the information processing apparatus comprising:

a treatment effect prediction model construction unit that constructs a treatment effect prediction model that includes the treatment method output model as a component, wherein the treatment effect prediction model comprises a shared network, a DTx network, and a standard treatment network, wherein the DTx network outputs a predicted value of the treatment effect when the treatment method output from the treatment method output model is used, the standard treatment network outputs a predicted value of the treatment effect when the treatment method is not used, and the shared network outputs parameters shared between the DTx network and the standard treatment network, and compares a treatment effect when the treatment method is used with a treatment effect when the treatment method is not used; and a model adjustment unit that generates a prediction model group by inactivating a weighting factor of the treatment effect prediction model based on a Bernoulli distribution calculated from entropy of a tendency score, wherein the weighting factor is inactivated for each of the shared network, the DTx network, and the standard treatment network when the treatment method is used and when the treatment method is not used, and adjusts the treatment method output model that is the component of the treatment effect prediction model such that a variance of a treatment effect output from the prediction model group falls within a predetermined range.

2. The information processing apparatus according to claim 1, wherein the model adjustment unit displays a variance of a treatment effect when the treatment method output from the adjusted treatment method output model is used.

3. The information processing apparatus according to claim 2, wherein the model adjustment unit further displays a variance of a treatment effect output from the treatment effect prediction model.

4. The information processing apparatus according to claim 1, wherein the model adjustment unit adjusts the treatment method output model when new data is collected.

5. The information processing apparatus according to claim 1, wherein the treatment effect prediction model construction unit inactivates the weighting factor of the treatment effect prediction model based on the Bernoulli distribution calculated from entropy of the tendency score when the treatment method is used and when the treatment method is not used.

6. The information processing apparatus according to claim 1, further comprising: a computation unit that loads a program stored in a storage unit and data necessary for executing the program into a memory, and executes the program to perform the construction of the treatment effect prediction model and the adjustment of the treatment method output model.

7. The information processing apparatus according to claim 1, wherein the treatment method output model is a neural network constructed by machine learning of known data.

8. The information processing apparatus according to claim 1, further comprising a network adapter for connecting to an electronic medical record and a digital therapy via a network, wherein the treatment method output model is transmitted from the digital therapy.

9. The information processing apparatus according to claim 1, wherein the tendency score is calculated using a logistic function based on coefficients calculated from collected data, a patient profile, and a patient state.

10. The information processing apparatus according to claim 1, wherein the treatment effect prediction model construction unit adjusts a coefficient of the treatment effect prediction model based on a loss function using a square error function, and uses a stochastic gradient method to adjust the coefficient.

11. The information processing apparatus according to claim 1, wherein the model adjustment unit deletes the standard treatment network from the treatment effect prediction model to construct a treatment effect prediction model used to adjust the treatment method output model.

12. The information processing apparatus according to claim 1, wherein the model adjustment unit adjusts coefficients of the treatment method output model based on a loss function regarding the variance of a predicted value output from the prediction model group such that the variance of the predicted value becomes smaller.

13. The information processing apparatus according to claim 1, wherein the model adjustment unit determines whether an end condition is satisfied, wherein the end condition is a predetermined number of repetitions, a threshold value for an output of a loss function, or a threshold value for an amount of change in the output of the loss function.

14. The information processing apparatus according to claim 1, wherein the model adjustment unit inputs a patient profile and a patient state of newly collected data to each of the prediction model group and outputs a predicted value of the treatment effect.

15. The information processing apparatus according to claim 7, wherein the neural network includes an activation function applied to outputs of the shared network, the DTx network, and the standard treatment network.

16. The information processing apparatus according to claim 2, further comprising a display device, wherein the model adjustment unit displays the variance of the treatment effect in a graph form in which a vertical axis indicates a frequency and a horizontal axis indicates an amount of effect.

17. The information processing apparatus according to claim 1, further comprising a display device that displays a model update start button, wherein the model adjustment unit adjusts the treatment method output model in response to the model update start button being pressed when new data is collected.

18. The information processing apparatus according to claim 1, further comprising a network adapter, wherein the adjusted treatment method output model is transmitted via a network to update a model of a digital therapy.

19. The information processing apparatus according to claim 1, further comprising a storage unit that stores the treatment effect prediction model and data necessary for constructing the treatment effect prediction model.

20. The information processing apparatus according to claim 3, wherein the model adjustment unit displays a treatment effect obtained by the treatment method output model before adjustment and a treatment effect obtained by the treatment method output model after adjustment together on a display device.

* * * * *